United States Patent
Keller

(10) Patent No.: US 9,730,752 B2
(45) Date of Patent: Aug. 15, 2017

(54) SURGICAL CLIP DEVICE

(71) Applicant: Aesculap AG, Tuttlingen (DE)

(72) Inventor: Anton Keller, Duerbheim (DE)

(73) Assignee: Aesculap AG, Tuttlingen (DE)

( * ) Notice: Subject to any disclaimer, the term of this patent is extended or adjusted under 35 U.S.C. 154(b) by 257 days.

(21) Appl. No.: 13/788,405

(22) Filed: Mar. 7, 2013

(65) Prior Publication Data

US 2013/0178880 A1    Jul. 11, 2013

Related U.S. Application Data

(63) Continuation of application No. PCT/EP2011/066125, filed on Sep. 16, 2011.

(30) Foreign Application Priority Data

Sep. 23, 2010 (DE) ........................ 10 2010 037 748

(51) Int. Cl.
| | |
|---|---|
| *A61B 17/08* | (2006.01) |
| *A61B 18/14* | (2006.01) |
| *A61B 17/122* | (2006.01) |
| *A61B 17/128* | (2006.01) |
| A61B 17/064 | (2006.01) |
| A61B 17/00 | (2006.01) |

(52) U.S. Cl.
CPC ........ *A61B 18/1447* (2013.01); *A61B 17/122* (2013.01); *A61B 17/1285* (2013.01); *A61B 17/064* (2013.01); *A61B 2017/00477* (2013.01); *A61B 2017/00929* (2013.01); *A61B 2018/145* (2013.01); *Y10S 227/902* (2013.01)

(58) Field of Classification Search
CPC .............. A61B 18/1442; A61B 17/122; A61B 17/0643; A61B 17/115; A61B 18/1447; A61B 2017/00929; A61B 17/1285; A61B 17/064; Y10S 227/902
USPC .................................................... 606/50, 157
See application file for complete search history.

(56) References Cited

U.S. PATENT DOCUMENTS

| 2,758,302 A | 8/1956 | White |
|---|---|---|
| 3,856,016 A | 12/1974 | Davis |

(Continued)

FOREIGN PATENT DOCUMENTS

| DE | 2405390 | 8/1975 |
|---|---|---|
| DE | 26 39 956 | 3/1978 |

(Continued)

OTHER PUBLICATIONS

Leaflet of Aesculap AG & Co. KG "Titanium Ligature Clips and Applicators", 8 pages, Feb. 2002.

(Continued)

*Primary Examiner* — Christopher D Koharski
*Assistant Examiner* — Pamela M Bays
(74) *Attorney, Agent, or Firm* — Lipsitz & McAllister, LLC

(57) ABSTRACT

In order to provide a surgical clip device with which the closure of vessels is successfully achieved even more safely, particularly in neurosurgery, it is proposed that the surgical clip device be provided with at least two electrically conductive clip parts that are electrically isolated from each other (by an element) and are arranged at a predetermined distance opposite each other.

14 Claims, 6 Drawing Sheets

(56) References Cited

U.S. PATENT DOCUMENTS

| | | | |
|---|---|---|---|
| 3,954,108 A | 5/1976 | Davis | |
| 4,137,919 A | 2/1979 | Farin et al. | |
| 4,569,346 A * | 2/1986 | Poirier | A61B 17/122 606/143 |
| 5,026,379 A * | 6/1991 | Yoon | A61F 6/206 606/141 |
| 5,160,339 A | 11/1992 | Chen et al. | |
| 5,171,250 A | 12/1992 | Yoon | |
| 5,201,900 A * | 4/1993 | Nardella | 606/157 |
| 5,217,473 A | 6/1993 | Yoon | |
| 5,366,459 A | 11/1994 | Yoon | |
| 5,441,509 A * | 8/1995 | Vidal | A61B 17/122 24/115 A |
| D371,390 S | 7/1996 | Johnson | |
| 5,609,599 A | 3/1997 | Levin | |
| 5,779,720 A | 7/1998 | Walder-Utz et al. | |
| 5,788,716 A | 8/1998 | Kobren et al. | |
| D401,626 S | 11/1998 | Shyu | |
| 6,015,417 A | 1/2000 | Reynolds, Jr. | |
| 6,428,548 B1 | 8/2002 | Durgin et al. | |
| 7,207,997 B2 | 4/2007 | Shipp et al. | |
| 7,572,266 B2 | 8/2009 | Young et al. | |
| D600,749 S | 9/2009 | Azman et al. | |
| D600,750 S | 9/2009 | Azman et al. | |
| 7,678,125 B2 | 3/2010 | Shipp | |
| 2004/0147942 A1 | 7/2004 | Chao | |
| 2006/0212049 A1 | 9/2006 | Mohiuddin | |
| 2007/0112365 A1* | 5/2007 | Hilal et al. | 606/157 |
| 2008/0147092 A1* | 6/2008 | Rogge | A61B 17/1285 606/142 |
| 2008/0312670 A1 | 12/2008 | Lutze et al. | |
| 2011/0224701 A1* | 9/2011 | Menn | A61B 17/122 606/151 |

FOREIGN PATENT DOCUMENTS

| | | |
|---|---|---|
| DE | 195 20 158 | 10/1998 |
| DE | 202006000329 | 4/2006 |
| DE | 10 2006 001 344 | 7/2007 |
| EP | 0567965 | 11/1993 |
| JP | 2009523044 | 6/2009 |
| WO | 9818389 | 5/1998 |

OTHER PUBLICATIONS

Brochure of Aesculap AG & Co. KG "Challenger Ti", 12 pages, Feb. 2002.

* cited by examiner

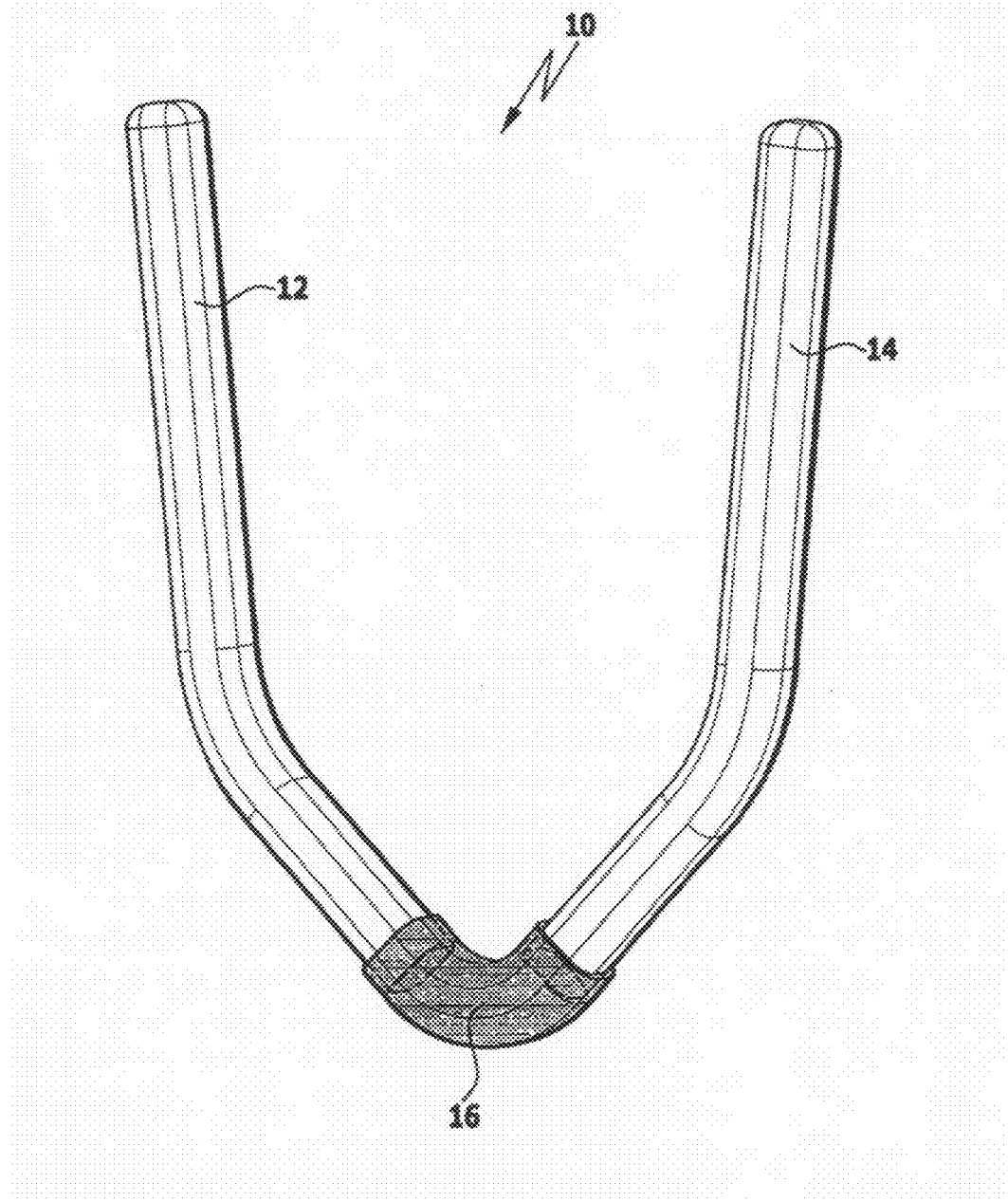

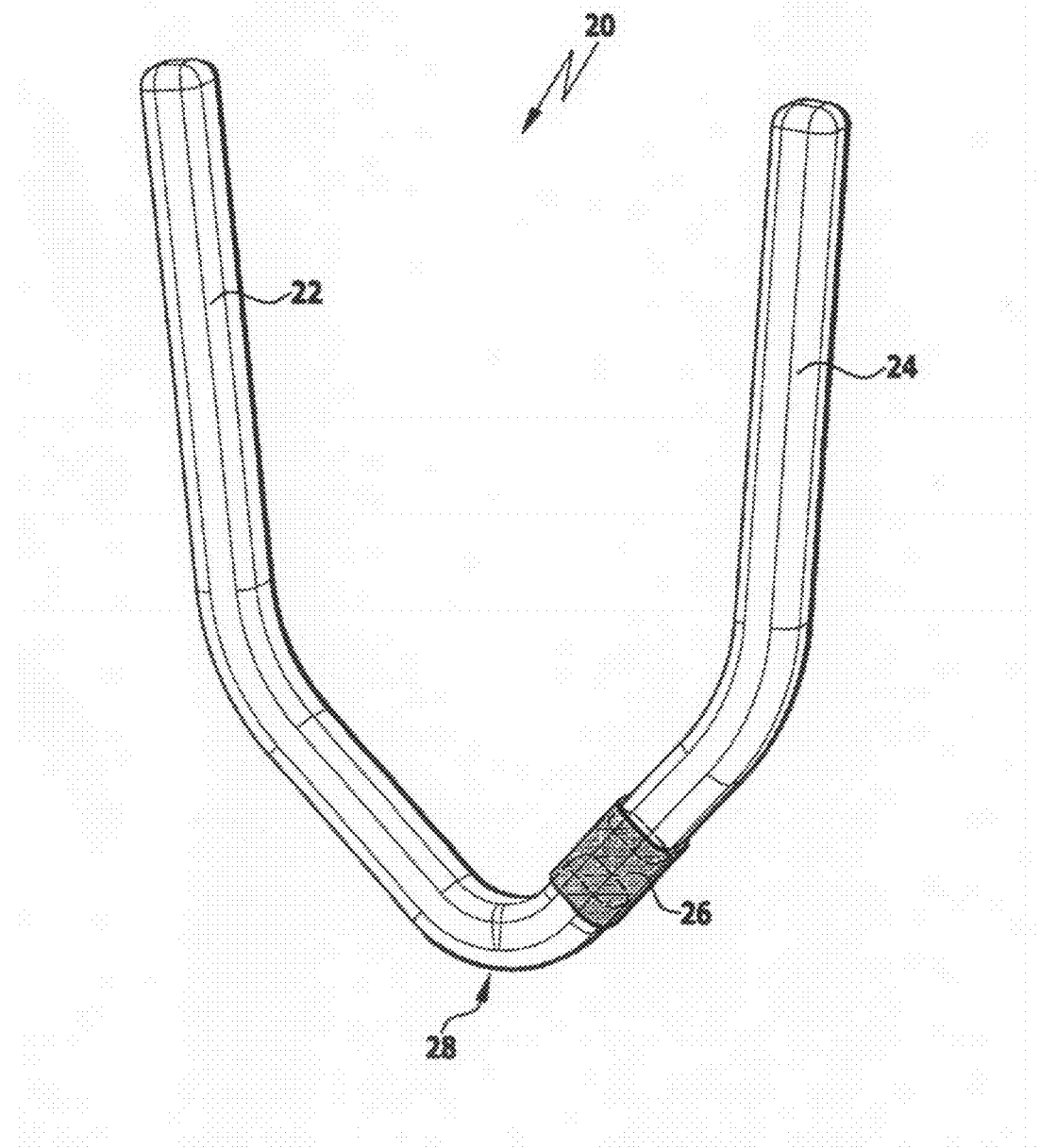

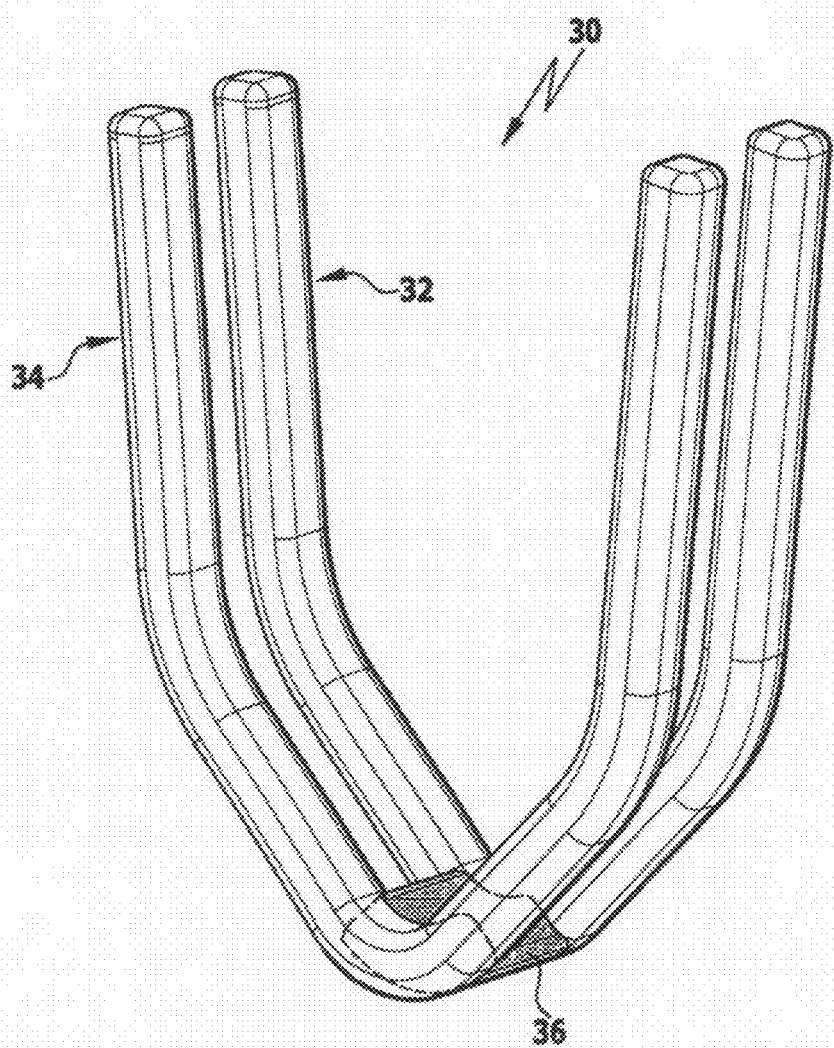

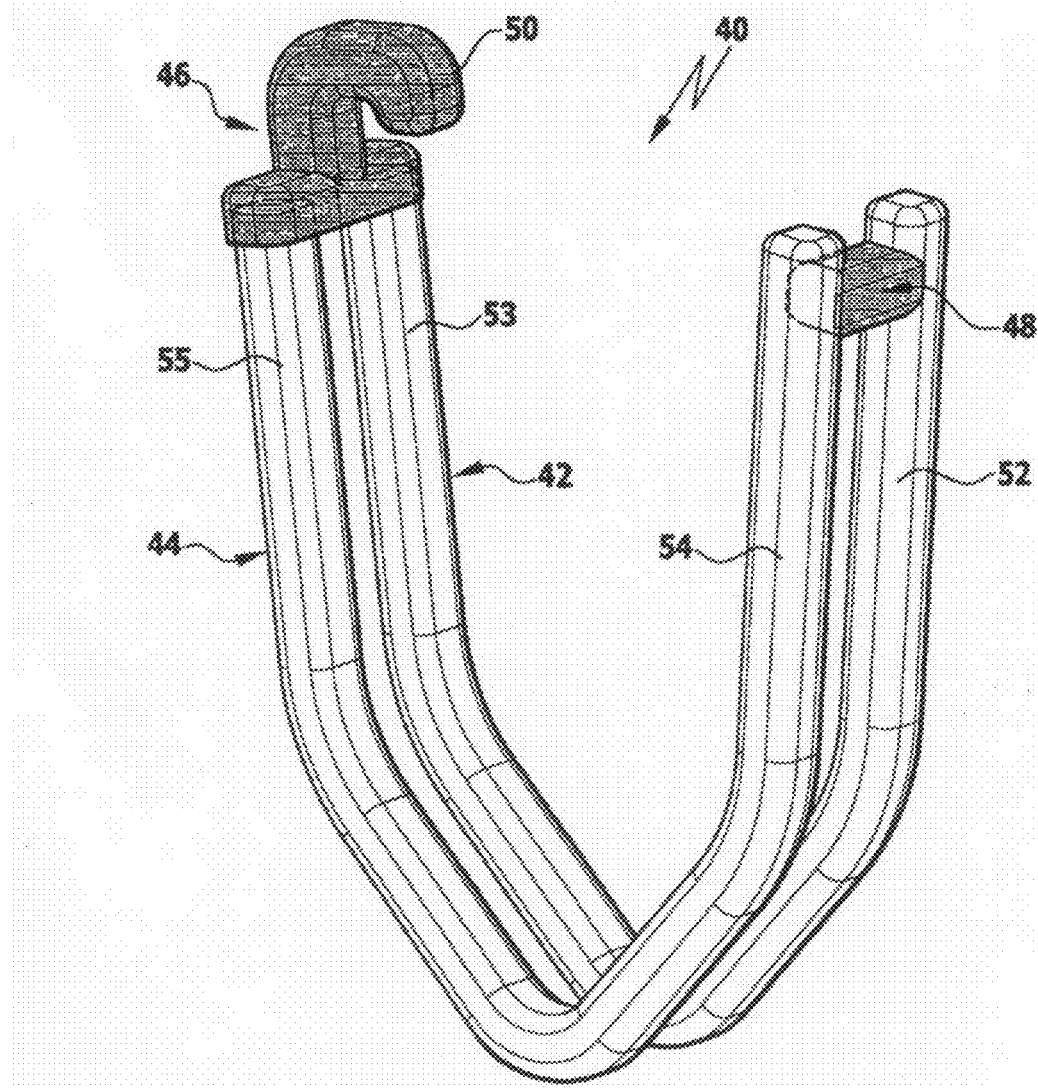

SURGICAL CLIP DEVICE

This application is a continuation of international application number PCT/EP2011/066125 filed on Sep. 16, 2011 and claims the benefit of German application number 10 2010 037 748.1 filed on Sep. 23, 2010, which are incorporated herein by reference in their entirety and for all purposes.

BACKGROUND OF THE INVENTION

The invention relates to a surgical clip device, in particular for closing vessels in neurosurgery.

To this end, metallic clips formed in a U-shape or V-shape are widely used, these clips being placed on the vessel with a clip applying forceps and, when deformed through the closing force of the forceps, effecting closure of the vessel concerned. Such clips are known for example from DE 195 20 158 C2.

In order to make more secure the closure of a vessel by a clip, so-called double-web clips have already been proposed (cf. for example DE 10 2006 001 344 A1) in which two U-shaped or V-shaped clamps of the clip that are formed integrally with each other and are arranged substantially parallel to each other form two points of closure at the vessel which are located one behind the other in a longitudinal direction of the vessel.

It can nevertheless still happen in critical situations that even such a double closure of the vessel does not prevent small leakages, thus still allowing small amounts of blood to leak therefrom.

It is an object of the invention to propose a surgical clip device with which the closure of vessels is successfully achieved even more safely, particularly in neurosurgery.

SUMMARY OF THE INVENTION

This object is attained by a surgical clip device as defined in claim 1.

Accordingly, the surgical clip device constructed in accordance with the invention relies not only on a mechanical closure of the vessel in which the two clip parts in the form of clamp arms, typically constructed of metal, hold the vessel in compression over its cross-section and thus close it shut, but owing to the clip parts or clamp arms being configured so as to be electrically isolated from each other, it is possible, concurrently with the application of the surgical clip device, to initiate a coagulation or sealing process in the area of the clip so that besides the mechanical closure a substance to substance-bonded closure of the vessel is additionally achieved.

An additional advantage is evident in that the coagulation and sealing process causes stiffening of the tissue in the coagulation region and as a result of this the clip device is additionally given more firm support. For that purpose, a clip applicator constructed in accordance with the invention is preferably used which will be described in more detail below.

The surgical clip device with its two electrically conductive clip parts, in particular clamp arms, arranged in electrical isolation from each other, can be implemented in a wide variety of embodiments.

In particular, the clip parts are part of a U-shaped or V-shaped clip configuration, wherein the two clip parts are held at a first end thereof on an electrically isolating holding part, thereby forming the two legs of the U-shaped or V-shaped configuration.

Preferably, the electrically isolating holding part is plastically deformable.

Typical materials used for the isolating holding parts are plastics materials.

Provision is in particular made for the two clip parts to be configured symmetrically with respect to one another, with the electrically isolating holding part being kept as small as possible in order to provide as large a sphere of action as possible for the coagulation process occurring through the electrically conductive clip parts.

In particular, the two clip parts are of substantially identical configuration and are arranged in a mirror image relationship with their first end fixed to the electrically isolating holding part.

Alternatively, the electrically isolating holding part can be located asymmetrically on the U-shaped or V-shaped clip so that a first clip part or clamp arm comprises the one leg and the central arcuate part, while the electrically isolating holding part and the second clip part or clamp arm form the other leg. Here, the plastic deformation does not inevitably occur on the holding part but takes place primarily on the central arcuate part of the one clip part, which typically consists of a metal material.

In a more preferred embodiment of the surgical clip device constructed in accordance with the invention, provision is made for the clip parts or clamp arms to be capable of being connected together at their respective free end opposite the first end thereof by way of an electrically isolating connection.

The connection is preferably configured as a latched connection.

To this end, it is in particular provided for electrically isolating latch elements to be arranged at the free ends of the clip parts, said latch elements latching into engagement with each other upon mechanical closure of the clip, thus already providing additional mechanical fixing of the clip at the vessel that is to be closed off.

As an alternative to the latched connection, provision may also be made for the electrically isolating connection to be a substance to substance-bonded connection forming at the free ends of the clip parts as a result of heat generated during the coagulation and sealing process.

In another embodiment of the surgical clip devices constructed in accordance with the invention, provision may be made for two clip parts, each of substantially U-shaped or V-shaped configuration, to be held in parallel alignment with each other and spaced apart at a predetermined distance. For application to a vessel, said two clip parts are grasped by a clip applicator, said clip applicator comprising a gripping tool for the two clip parts having gripping jaws which are electrically isolated from each other. The two clip parts can then be applied to the vessel using the clip applicator, and in the same step a sealing action in the area of the mechanical closure of the vessel can be achieved by a coagulation current. Here, the coagulation procedure results in an additional closure of the vessel that is substance to substance-bonded.

The two clip parts may lack any connection to each other and just be held ready in a desired array, for example in a magazine, until received by the gripping tool. After withdrawal from the magazine and until application, the two clip parts are held in an electrically isolated and spaced-apart relationship to each other by the mutually electrically isolated gripping jaws.

More preferably, the two clip parts are releasably held in parallel alignment with each other and spaced apart at the predetermined distance in a holding device. In such clip devices constructed in accordance with the invention, the configuration of the gripping jaws of the clip applicator allows for a somewhat simpler design.

Alternatively, provision may be made for the two clip parts to be fixedly connected in parallel alignment with each other and spaced apart at the predetermined distance by an electrically isolating holder. The holder in turn can be made of a plastics material. In that case as well, the configuration of the gripping jaws of the clip applicator is simplified.

The holder can be of one-piece configuration and for example interconnect the two clip parts at the respective mid-regions thereof.

In a more preferred embodiment, the free ends of the two clip parts are in each case connected together by way of an electrically isolating holding part of the holder.

More preferably, said two holding parts of the holder can then also be configured in the form of latch elements which latch into engagement with each other when the clip is applied to the vessel.

As has already been described above, it may also be provided that, in lieu of the latch elements, electrically isolating holding parts be used that together form a substance-to-substance bond by heat generated during the coagulation and the sealing of the vessel.

Also in this case, the free clip ends are fixedly connected to each other, and thus the vessel, besides being mechanically secured by the double clip device as described above, is additionally sealed via the coagulation procedure.

The invention further relates to a clip applicator for use with a surgical clip device constructed in accordance with the invention, as described above.

The applicator constructed in accordance with the invention comprises a gripping tool having two mutually electrically isolated gripping jaws for the two clip parts, wherein the gripping jaws are capable of being connected to a coagulation current-delivering current source.

More preferably, the applicator comprises a magazine having a clip carrier, wherein the clip carrier has a plurality of surgical clip devices arranged thereon as described above.

The current source with which the gripping jaws of the applicator can be connected is preferably a high-frequency current source.

These and further advantages of the invention are described in more detail below with reference to the drawings.

BRIEF DESCRIPTION OF THE DRAWINGS

FIGS. 1A, 1B show two variants of a first embodiment of a surgical clip device constructed in accordance with the invention;

FIGS. 2A, 2B show two variants of a second embodiment of a surgical clip device constructed in accordance with the invention;

DETAILED DESCRIPTION OF THE INVENTION

Figure 3:
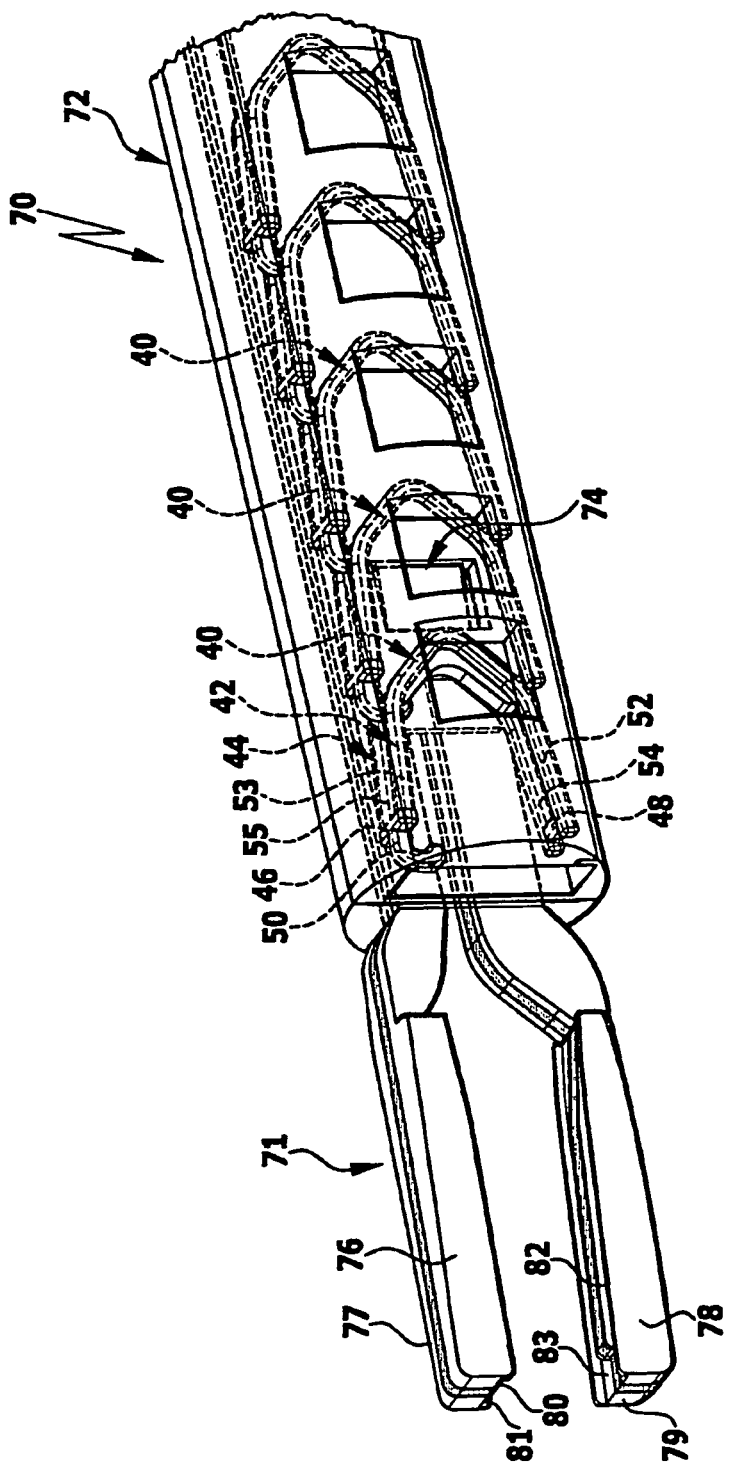
FIG. 3 illustrates a clip applicator constructed in accordance with the present invention.

FIG. 1A shows a surgical clip device 10 (hereinafter also referred to as clip) having two electrically conductive clip parts or clamp arms in the form of legs 12 and 14 which are held in a substantially U-shaped arrangement in electrical isolation from each other by a holding part 16 and are held spaced apart at a predetermined distance from each other and in opposed relationship with respect to each other. When the clip 10 is applied to a vessel, the two legs 12 and 14 are urged toward each other from two sides of the vessel and are maintained electrically isolated from each other by way of the holding part 16. The holding part is fabricated from a plastically deformable plastics material so that applying the clip 10 results in a permanent mechanical closure of the vessel. In the compressed state, a coagulation current is then applied via a gripping tool of an applicator so that the vessel, apart from being mechanically closed shut, is additionally sealed off.

The clip device 20 depicted in FIG. 1B has asymmetrically configured clamp arms in the form of legs 22, 24 and an electrically isolating holding part 26 correspondingly arranged in an off-centre position.

When the clip 20 is applied, plastic deformation takes place primarily on an arcuate part 28 integrally formed on the leg 22, thereby providing for a permanent mechanical closure of the vessel.

FIG. 2A shows a surgical clip device 30 in which two clip parts or clamp arms 32, 34, each of substantially U-shaped configuration, are arranged parallel to each other. These two clip parts can, for example at a mid-region thereof, be joined together, and held in a spaced-apart relationship, by a web 36 made of an electrically isolating material, such as a plastics material.

A more preferred clip device, however, is a clip device 40 illustrated in FIG. 2B in which two U-shaped clip parts or clamp arms 42, 44 are, at their respective free ends 52,53; 54,55, held in electrically isolated and spaced-apart relationship via two holding parts 46, 48, with the holding part 46 being preferably provided with a latch element 50 that is of hook-shaped configuration in FIG. 2B and is connectable to the holding part 48 in a form-locked manner.

Alternatively or additionally, provision may be made for the material of the holding parts 46, 48 or in particular also of the latch part 50 to be selected such that the heat generated from coagulation of the vessel material is sufficient to effect a substance-to-substance bond between the holding parts 46, 48, in particular between the part designated 50 and the part designated 48.

FIG. 3 illustrates a clip applicator 70 constructed in accordance with the invention, wherein the portion of the handle for operating the applicator 70 is omitted for simplicity.

Shown in FIG. 3 is a shaft 72 of the applicator 70, said shaft 72 having arranged therein a clip magazine 74 with clips 40 situated in a row one behind the other. The shaft 72 has on its distal end a gripping tool 71 comprising two gripping jaws 76, 77 and 78, 79 held in electrically isolated relationship from each other and which, when a clip 40 is applied, receive and guide, in receiving grooves 80, 81; 82, 83 thereof, the clip parts 42, 44 of the clip 40 with the free ends 52, 53; 54, 55 thereof.

Once a clip 40 has been positioned at a vessel using the gripping tool 71, the gripping jaws 76, 77; 78, 79 can be pivoted relative to one another by a handle (not shown) of the applicator 70 so that the clip 40 is squeezed together, which first results in a double mechanical closure of the vessel; this will be explained in greater detail in conjunction with the schematic drawings of FIGS. 4A to 4D.

Because the gripping jaws 76, 77; 78, 79 of the clip applicator 70 are held in electrically isolated relationship, a current may then be applied to them, and the physical contact established between the free ends of the legs 52, 53;

54, 55 of the clip 40 and the gripping jaws 76, 77; 78, 79 also establishes an electrically conductive contact therebetween so that the electric current can be delivered to the legs of the clip 40.

The sequence of steps for applying a clip device constructed in accordance with the invention is schematically shown in FIGS. 4A to 4D, taking as an example the clip device 40 constructed in accordance with the invention as illustrated in FIG. 2B. The procedure applies analogously to the clips of FIGS. 1A, 1B and 2A.

Figure 4A:
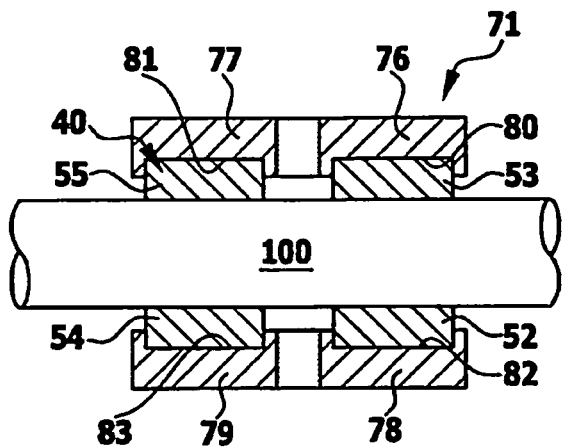
FIGS. 4A to 4D show schematically a sequence of steps in the process of applying a clip device constructed in accordance with FIG. 2A or 2B.

FIG. 4A is a sectional view of the clip 40 with its legs 52, 54 located below a vessel 100 and legs 53, 55 located above the vessel 100. The legs 52, 54 are guided and held in grooves 82, 83 of the gripping jaws 78, 79, and the legs 53, 55 are guided and held in grooves 80, 81 of the gripping jaws 76, 77.

Figure 4B:
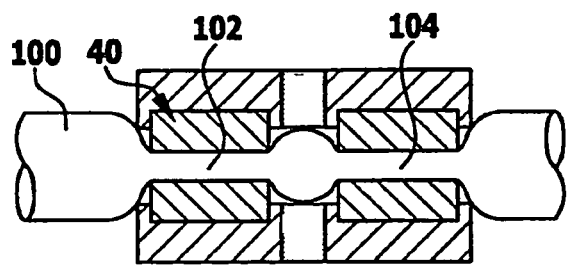

In the next step, as shown in FIG. 4B, the gripping jaws 76, 77 and 78, 79 are moved toward each other, thereby approximating the legs 52, 54 and 53, 55 toward each other, thereby mechanically closing the vessel 100 in the regions 102 and 104 thereof, said regions 102 and 104 being spaced apart in a longitudinal direction of the vessel.

In the closed position of the clip 40, the part designated 50 then latches into engagement with the holding part 48, thus securing the closed position of the clip 40.

Figure 4C:
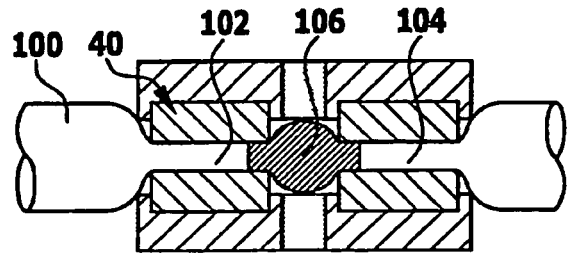

Subsequently, the gripping jaws 76, 78 and 77, 79 are connected in pairs to a terminal of a HF current source so that a coagulated region 106 of the vessel 100 then forms between the mechanically closed-off regions 102, 104 of the vessel 100 (cf. FIG. 4C).

Figure 4D:
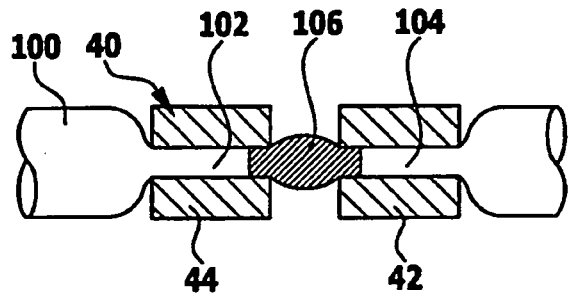

As soon as the coagulation procedure is complete, which typically only takes few seconds/the fraction of a second, the gripping jaws 76, 77; 78, 79 are returned to their initial position and the applicator 70 is removed from the vessel 100. This leaves the vessel 100 with the legs 52, 53 and 54, 55 of the clip 40 applied to the vessel 100 and mechanically interlocked via the holding parts 46, 48, 50, wherein in addition to the double mechanical closure of the vessel 100 in the regions 102, 104, additional safety is provided by a coagulated region 106 (FIG. 4D).

The invention claimed is:

1. Surgical clip device for closing vessels, comprising:
two electrically conductive clip parts arranged in electrical isolation from each other and spaced apart at a predetermined distance opposite each other;
each of the two clip parts having a substantially U-shaped or V-shaped configuration and being held in parallel alignment with each other at the predetermined distance, and
each of the two clip parts having two respective free ends, wherein:
the two respective free ends of each clip part are adapted to be moved towards one another during an application procedure to form two clamping regions in a vessel to be closed, the two clamping regions being spaced apart at the predetermined distance, and
in a closed position of the clip, each of the free ends of the two clip parts are configured to apply a coagulation current to the vessel so as to form a coagulated region of the vessel extending continuously between the two spaced apart clamping regions.

2. Surgical clip device in accordance with claim 1, wherein each of the two clip parts are held with a first free end of the two free ends thereof on an electrically isolating holding part.

3. Surgical clip device in accordance with claim 2, wherein the two clip parts have a substantially mirror image configuration relative to one another and are each symmetrically held with the first free end thereof on the electrically isolating holding part.

4. Surgical clip device in accordance with claim 2, wherein the two free ends of the respective clip parts opposite the first free ends thereof are connectable to each other by way of an electrically isolating latched connection.

5. Surgical clip device in accordance with claim 1, wherein the two clip parts are releasably held in parallel alignment with each other and spaced apart at the predetermined distance in a holding device.

6. Surgical clip device in accordance with claim 1, wherein the two clip parts are fixedly connected in parallel alignment with each other and spaced apart at the predetermined distance by an electrically isolating holder.

7. Surgical clip device in accordance with claim 6, wherein the holder comprises a first holding part which fixedly connects the two clip parts.

8. Surgical clip device in accordance with claim 7, wherein the holder further comprises a second holding part, wherein the first holding part connects first ones of each of the two free ends of the respective clip parts which are adjacent one another and the second holding part fixedly connects second ones of the two free ends of the respective clip parts which are adjacent one another.

9. Surgical clip device in accordance with claim 8, wherein the first and second holding parts are connectable to each other.

10. Surgical clip device in accordance with claim 9, wherein the first and second holding parts are releasably connectable to each other.

11. Surgical clip device in accordance with claim 9, wherein the first and second holding parts are latchingly connectable to each other.

12. Clip applicator for use with a surgical clip device, the surgical clip device comprising:
two electrically conductive clip parts arranged in electrical isolation from each other and spaced apart at a predetermined distance opposite each other,
each of the two clip parts having a substantially U-shaped or V-shaped configuration and being held in parallel alignment with each other at the predetermined distance, and
each of the two clip parts having two respective free ends,
wherein the two respective free ends of each clip part are adapted to be moved towards one another during an application procedure to form two clamping regions in a vessel to be closed, the two clamping regions being spaced apart at the predetermined distance, and
the applicator comprising a gripping tool having mutually electrically isolated gripping jaws for the two clip parts, wherein:
the gripping jaws are connectable to a coagulation current-delivering current source, and
in a closed position of the clip, the coagulation current-delivering current source applies a coagulation current to each of the free ends of the two clip parts such that each of the free ends of the two clip parts apply the coagulation current to the vessel, forming a coagulated region of the vessel extending continuously between the two spaced apart clamping regions.

13. Clip applicator in accordance with claim 12, wherein the applicator comprises a magazine having a clip carrier, wherein the clip carrier has arranged thereon a plurality of surgical clip devices.

14. Clip applicator in accordance with claim 12, wherein the current source is a high-frequency current source.

\* \* \* \* \*